United States Patent
Haas et al.

(10) Patent No.: US 10,542,747 B2
(45) Date of Patent: Jan. 28, 2020

(54) PLANT IRRIGATION METHODS WITH 1-MCP

(75) Inventors: Ulrich Johannes Haas, Stein (CH); Christophe Weider, Stein (CH); Ronald Zeun, Stein (CH); David Charles Ross, Greensboro, NC (US); Daniel Warden Kidder, Greensboro, NC (US); Yueqian Zhen, Philadelphia, PA (US); Tim Malefyt, Spring House, PA (US)

(73) Assignee: Syngenta Participations AG, Basel (CH)

( * ) Notice: Subject to any disclaimer, the term of this patent is extended or adjusted under 35 U.S.C. 154(b) by 145 days.

(21) Appl. No.: 13/701,711

(22) PCT Filed: Jun. 3, 2011

(86) PCT No.: PCT/US2011/039086
§ 371 (c)(1),
(2), (4) Date: Jul. 22, 2013

(87) PCT Pub. No.: WO2011/153445
PCT Pub. Date: Dec. 8, 2011

(65) Prior Publication Data
US 2013/0298290 A1    Nov. 7, 2013

(30) Foreign Application Priority Data
Jun. 4, 2010 (EP) ................................. 10005802

(51) Int. Cl.
| | | |
|---|---|---|
| *A01N 27/00* | (2006.01) | |
| *A01N 25/02* | (2006.01) | |
| *A01N 25/12* | (2006.01) | |
| *A01N 25/22* | (2006.01) | |
| *A01N 43/82* | (2006.01) | |
| *A01N 37/08* | (2006.01) | |
| *A01N 43/54* | (2006.01) | |
| *A01N 43/653* | (2006.01) | |
| *A01N 43/88* | (2006.01) | |

(52) U.S. Cl.
CPC ............ *A01N 27/00* (2013.01); *A01N 25/02* (2013.01); *A01N 37/08* (2013.01); *A01N 43/54* (2013.01); *A01N 43/653* (2013.01); *A01N 43/82* (2013.01); *A01N 43/88* (2013.01)

(58) Field of Classification Search
CPC ................................ A01N 25/02; A01N 27/00
USPC .......................................................... 504/357
See application file for complete search history.

(56) References Cited

U.S. PATENT DOCUMENTS

| | | | |
|---|---|---|---|
| 3,869,273 A * | 3/1975 | Noveroske .................... 504/190 |
| 7,098,170 B2 | 8/2006 | Asrar et al. | |
| 8,691,728 B2 * | 4/2014 | Kostansek ............. A01N 27/00 504/357 |
| 2001/0049373 A1 * | 12/2001 | Chalquest ..................... 514/269 |
| 2003/0207926 A1 * | 11/2003 | Armstrong et al. .......... 514/367 |
| 2007/0149401 A1 | 6/2007 | Haskell et al. | |
| 2007/0265166 A1 * | 11/2007 | Bardella et al. .............. 504/357 |
| 2009/0186762 A1 | 7/2009 | Rademacher et al. | |
| 2009/0192040 A1 | 7/2009 | Grobler et al. | |
| 2010/0009852 A1 | 1/2010 | Rosinger et al. | |
| 2010/0218278 A1 | 8/2010 | Kaster et al. | |

FOREIGN PATENT DOCUMENTS

CN          101715760       *   6/2010

OTHER PUBLICATIONS

Derwent abstract 2010-G98758, abstracting CN 101715760 (Jun. 2, 2010).*
Machine translation of CN 101715760 (Jun. 2, 2010).*
FAO specifications and evaluations for agricultural pesticides, 1-methylcyclopropene, Food and Agriculture Organization of The United Nations, 2010, retrieved from the Internet on Feb. 2, 2019:< http://www.fao.org/fileadmin/templates/agphome/documents/Pests_Pesticides/Specs/1-MCP10.pdf >.*
SmartFresh label application by AgroFresh Inc., U.S. Environmental Protection Agency, 2010, pp. 1-23.*
Hiller, J. et al., "Chemigation Practices for Wyoming," University of Wyoming Cooperative Extension Service, B-1024, pp. 1-8 (1995).*
Kawakami et al., "Physiological Effects of 1-Methylcyclopropene on Well-Watered and Water-Stressed Cotton Plants", Jan. 20, 2010, Journal of Plant Growth Regulation, vol. 29, Is 3, pp. 280-288.

* cited by examiner

*Primary Examiner* — John Pak
(74) *Attorney, Agent, or Firm* — Baker & Hostetler, LLP; Toni-Junell Herbert

(57) ABSTRACT

The present invention is directed to novel methods of increasing the abiotic environmental stress tolerance of a plant, to methods of improving the quality and/or yield of a plant crop, to methods of application of a cyclopropene such as 1-MCP to a plant, and to crops produced using said methods.

8 Claims, 1 Drawing Sheet

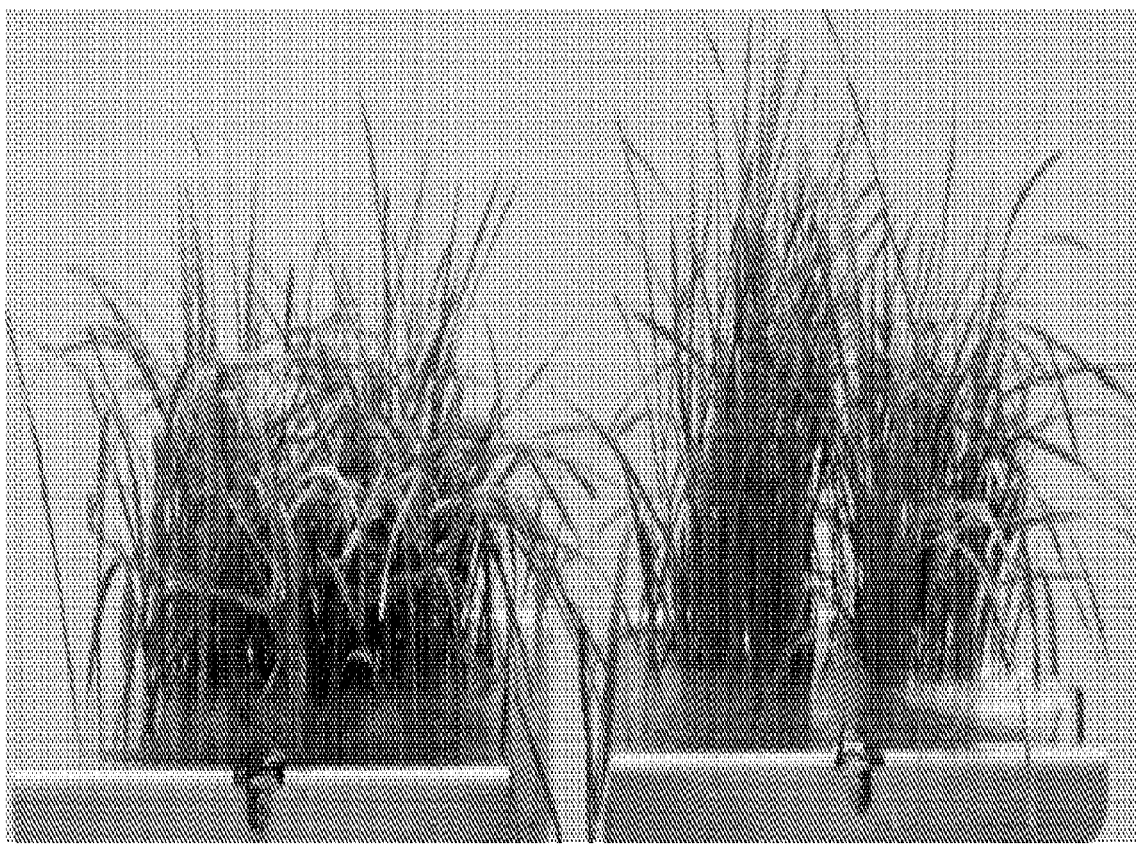

PLANT IRRIGATION METHODS WITH 1-MCP

This application is a 371 of International Application No. PCT/US2011/039086 filed Jun. 3, 2011, which claims priority to EP 10005802.3 filed Jun. 4, 2010, the contents of which are incorporated herein by reference.

FIELD OF THE INVENTION

The present invention is directed to methods of increasing the environmental stress tolerance of a plant, to methods of improving the quality and/or yield of a plant crop, to methods of application of agrochemicals having a physiological effect on a plant, and to crops produced using said methods.

BACKGROUND

The agrochemical industry is continually seeking methods of improving the growth of plants. Chemicals are typically used to control undesirable species, such as insects or vegetation (e.g. weeds or fungi) and to promote plant growth (e.g., by providing nutrients), thereby improving the growth of plants.

Aside from the direct damage caused by external factors such as plant pests, or the lack of nutrients, the growth of a plant is affected, often detrimentally, by the plant's own responses to external environmental stress factors. When subjected to such stress factors plants display a variety of mechanistic responses as protective measures, with a resultant adverse effect on growth, development, and productivity. Significant losses in quality and yield are commonly observed.

One of the key responses displayed by plants in response to stress is the production of the plant hormone ethylene, which causes a variety of plant physiological effects, such as senescence, inhibition of root growth and inhibition of stem growth. Ethylene also acts to accelerate the process of fruit ripening, flower-opening and leaf abscission. The synthetic plant growth regulator 1-methylcyclopropene (1-MCP) blocks the effects of ethylene and is used commercially to delay fruit-ripening in stored fruits and vegetables and maintaining the freshness of cut flowers, potted flowers, bedding, nursery and foliage plants. The compound is a gas and must be used in enclosed spaces to be effective. It is approved in the USA and elsewhere for use in enclosed spaces, such as greenhouses, store rooms, coolers, enclosed truck trailers, controlled atmosphere food storage facilities, and shipping containers. It is also being developed as post-emergence spray in efforts to protect field crops during extended periods of extreme temperatures, drought and other stresses (Farm Industry News, Jan. 18, 2008).

European patent EP 0,220,514 refers to compositions comprising phytohormones and their use in methods for increasing the quantity and quality of fruits or flowers of plants in horticulture or agriculture. International patent application WO 2005/018319 refers to the application of auxins to the roots of plants by drip irrigation or spray application in order to inhibit insect infestation.

There is a need for additional methods for dealing with the environmental stresses experienced by plants in order to increase their tolerance thereto, and to improve the quality and yield of a plant crop subject to those stresses.

SUMMARY OF THE INVENTION

It has surprisingly been found that the application of at least one cyclopropene having a physiological effect on a plant, in the irrigation water, increases the tolerance of the plant to environmental stresses resulting in a plant crop having an improved quality and/or in an increased yield.

Accordingly, in a first aspect, the present invention provides a method of increasing the environmental stress tolerance of a plant comprising the application of at least one cyclopropene in the plant irrigation water wherein said cyclopropene has a physiological effect on the plant.

BRIEF DESCRIPTION OF THE DRAWING

Having thus described the invention in general terms, reference will now be made to the accompanying drawing wherein:

FIG. 1 illustrates wheat plants grown in pouches. On the right-hand side plants treated with 1-MCP and on the left-hand side non treated check plants.

DETAILED DESCRIPTION

In one embodiment, suitable cyclopropenes are gaseous at ambient temperature and are selected from a compound of formula I:

wherein n is a number from 1 to 4, suitably n is a number from 1 to 2, and most suitably n is 1. The variable group R is selected from hydrogen, saturated or unsaturated $C_1$ to $C_4$ alkyl, hydroxy, halogen, alkoxy, amino and carboxy. In one embodiment, R is methyl.

In one embodiment, the cyclopropene gas is selected from cyclopropene, dimethylcyclopropene and 1-methylcyclopropene (1-MCP).

In one embodiment, the 1-methylcyclopropene may be applied as a sole ingredient, or alternatively, may be in the form of an agrochemical composition comprising an agrochemically acceptable diluent or carrier. References herein to 1-methylcyclopropene or components comprising said compounds shall be deemed to include 1-methylcyclopropene as a sole ingredient or agrochemical compositions thereof.

In one embodiment, the 1-MCP is provided in an agrochemical composition comprising a suitable molecular encapsulating agent for the gaseous 1-MCP such as cyclodextrins including α-cyclodextrin.

The solid complex of the cyclopropene gas and a molecular encapsulating agent is sometimes referred to herein as a "cyclopropene complex".

For example, in one method of making a cyclopropene complex in which 1-MCP is encapsulated in a molecular encapsulating agent, the 1-MCP gas is bubbled through a solution of α-cyclodextrin in water, from which the complex first precipitates and is then isolated by filtration. Cyclopropene complexes made by the above method are isolated, dried and stored in solid form, for example as an active ingredient containing powder.

In a further aspect, the present invention provides a method of reducing damage to a plant caused by one or more environmental stress factors, comprising the application of 1-MCP in the plant irrigation water wherein 1-MCP has a physiological effect on the plant.

In a further aspect, the present invention provides a method for improving the quality of a plant crop comprising the application of 1-MCP in the plant irrigation water wherein said agrochemical has a physiological effect on the plant.

In a further aspect, the present invention provides a method for improving the yield of a plant crop comprising the application of 1-MCP in the plant irrigation water wherein said agrochemical has a physiological effect on the plant.

In a further aspect, the present invention provides a method of improving plant vigour comprising the application of 1-MCP in the plant irrigation water wherein said agrochemical has a physiological effect on the plant.

Controlling the amount of 1-MCP a plant receives is very difficult because it is a gas (b.p. <5° C.), which is commonly applied as a spray application. Its volatility provides for only a short residence time on a plant as evaporation is rapid. In consequence, maximum benefits cannot be achieved that would otherwise be the case with less volatile agrochemicals. A higher than desirable portion of the material is therefore wasted with undesirable losses to the environment.

It has surprisingly been found that the application of 1-MCP, in the irrigation water, increases the tolerance of the plant to environmental stresses. In particular, greater control over the amount of the material administered to the plant may be achieved. There is significantly less wastage and the risk of harm to the operator or the environment is reduced. The problems of spray drifting unintentionally onto other crops are eliminated.

Instead of repeated spraying of materials which is both labour-intensive and costly, much simpler, targeted, application is achieved. The concentration of 1-MCP in the irrigation water may be much lower than that of a spray and continuous, controlled, application can be achieved. Formulation problems are also reduced as effective concentrations may be achieved even though the water-solubility of 1-MCP is low (137 mg I–1). The quantities of agrochemicals transported to farms and within a farm are reduced, which in itself provides environmental benefits.

The concentration of 1-MCP in the water of irrigation may be from 1 to 1000 ppm, preferably 10 to 750 ppm, more preferably 50 to 500 ppm, yet more preferably from 100 to 250 ppm, for example 150, 175, 200 or 225 ppm. In another embodiment, 1-MCP use rates are about 0.1 to 50 g per hectare of cultivated crop under irrigation.

Accordingly, in a preferred embodiment, the present invention provides a method of increasing the environmental stress tolerance of a plant comprising the application of 1-methylcyclopropene in the plant irrigation water.

In a further preferred embodiment, the present invention provides a method of reducing damage to a plant caused by one or more environmental stress factors, comprising the application of 1-methylcyclopropene in the plant irrigation water.

In a further preferred embodiment, the present invention provides a method for improving the quality of a plant crop comprising the application of 1-methylcyclopropene in the plant irrigation water.

In a further preferred embodiment, the present invention provides a method for improving the yield of a plant crop comprising the application of 1-methylcyclopropene in the plant irrigation water.

In a further preferred embodiment, the present invention provides a method of improving plant vigour comprising the application of 1-methylcyclopropene in the plant irrigation water.

In a further aspect, the present invention provides a crop produced using a method of the present invention.

The methods of the present invention are applicable to any type of environmental stress that a plant may experience during its growth, including abiotic stress. The methods of the present invention are considered to be particularly suitable wherein the stress experienced by the plant is abiotic stress. In a preferred embodiment, the methods of the present invention are applicable when the abiotic stress experienced by a plant during its growth is drought, flood, excessive temperature, low temperature, frost, excess sunlight, insufficient sunlight, wind, inadequate soil nutrients, excessive soil salinity, air pollution, soil pollution or water pollution, or any combination thereof. Most preferably, the stress experienced is drought, excessive temperature or frost, or any combination thereof.

Accordingly, in a more preferred embodiment, the present invention provides a method of increasing the environmental stress tolerance of a plant comprising the application of 1-methylcyclopropene in the plant irrigation water, wherein the stress experienced is drought, excessive temperature or frost, or any combination thereof. Most preferably the stress experienced is drought.

In a further more preferred embodiment, the present invention provides a method of reducing damage to a plant caused by one or more environmental stress factors, comprising the application of 1-methylcyclopropene in the plant irrigation water, wherein the stress experienced is drought, excessive temperature or frost, or any combination thereof. Most preferably the stress experienced is drought.

In a further more preferred embodiment, the present invention provides a method for improving the quality of a plant crop comprising the application of 1-methylcyclopropene in the plant irrigation water, wherein the stress experienced is drought, excessive temperature or frost, or any combination thereof. Most preferably the stress experienced is drought.

In a further more preferred embodiment, the present invention provides a method for improving the yield of a plant crop comprising the application of 1-methylcyclopropene in the plant irrigation water, wherein the stress experienced is drought, excessive temperature or frost, or any combination thereof. Most preferably the stress experienced is drought.

In a further more preferred embodiment, the present invention provides a method of improving plant vigour comprising the application of 1-methylcyclopropene in the plant irrigation water, wherein the stress experienced is drought, excessive temperature or frost, or any combination thereof. Most preferably the stress experienced is drought.

The term "increasing the yield" of a plant means that the yield of a product of the plant is increased by a measurable amount over the yield of the same product of the plant produced under the same conditions, but without the application of the combinations according to the present invention. It is preferred that the yield is increased by at least about 0.5%, preferably 1%, more preferably 2%, yet more preferably 4% or more. Even more preferred is an increase in yield of at least about 5%, 10%, 15% or 20% or more.

The term "improving plant vigour" means that the vigour rating, or the plant weight, or the plant height, or the plant canopy, or the visual appearance, or any combination of these factors, is increased or improved by a measurable or noticeable amount over the same factor of the plant produced under the same conditions, but without the application of the combinations according to the present invention.

The use of the methods of the invention can be via any suitable irrigation method, which ensures that the one or more agrochemicals penetrate the soil the rhizosphere or is otherwise absorbed by the plant, for example, localised irrigation, spray irrigation, drip irrigation, bubbler irrigation, sub-soil irrigation, soil injection, seepage irrigation, surface irrigation, flooding, furrow, drench, application through sprinklers, micro-sprinklers or central pivot, or manual irrigation, or any combination thereof.

In a specific embodiment, there may be mentioned sprinkler, subsurface drip and surface drip irrigation.

The rate and frequency of application of the 1-methylcyclopropene according to the methods of the present invention may vary within wide limits and depends on the type of irrigation, the nature of the soil, the method of application, the plant to be controlled, the prevailing climatic conditions, and other factors governed by the method of application, the time of application and the target plant.

Typically, the application of 1-methylcyclopropene according to the methods of the present invention can occur on several occasions during the growth of a plant up to the harvest. The 1-methylcyclopropene may be applied once or on several occasions during the growth of a plant depending on the plant and circumstances, for example, 1 to 6 or 1 to 4 occasions, and the amounts indicated above for 1-methylcyclopropene are application rates are for each application.

The methods of the present invention may be used for the treatment of any plant including, for example, cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflower, soybean, jatropha, oil palm); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, for example, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annus* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutate* Gaud.), sheep fescue (*Festuca ovine* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.)).

The methods of the present invention are particularly suitable for the treatment of crops, such as field crops, fruits, vegetables, nuts (particularly peanuts), berries, tropical plantations, ornamentals and others, such as wheat, barley, rye, oats, rice, maize, sorghum, beans, lentils, peas, soybeans, rape, mustard, poppy, sugar- and fodder-beet, cotton, flax, hemp, jute, sunflowers, castor oil, groundnuts, potatoes, tobacco, sugar cane, apples, pears, plums, peaches, nectarines, apricots, cherries, oranges, lemons, grapefruit, mandarins, olives vines, hops, almonds, walnuts, hazelnuts, avocado, bananas, tea, coffee, coconut, cocoa, natural rubber plants, oil plants, strawberries, raspberries, blackberries, spinach, lettuce, asparagus, cabbages, Chinese kale, carrots, onions, tomatoes, cucumbers, pepper, eggplants, melons, paprika, chilli, roses, chrysanthemums and carnations. The plants may also be genetically modified.

The present invention may be used in all types of soil, including salty soils, low-high pH soils, sandy-, clay-, loamy, silty soils, low-, high organic matter soils. Suitable plants also include plants that have been rendered tolerant to herbicides like bromoxynil or classes of herbicides (such as HPPD inhibitors, ALS inhibitors; for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogenoxidase) inhibitors as a result of conventional methods of breeding or genetic engineering. An example of a crop that has been rendered tolerant to imidazolinones (e.g. imazamox) by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

Suitable plants also include plants which have been so transformed by the use of recombinant DNA techniques that they are capable of synthesising one or more selectively acting toxins, such as are known from toxin-producing bacteria, especially those of the genus *Bacillus*.

Suitable plants also include plants which have been so transformed by the use of recombinant DNA techniques that they are capable of synthesising antipathogenic substances having a selective action, such as the so-called "pathogenesis-related proteins" (PRPs, see e.g. European patent application EP 0,392,225). Examples of such antipathogenic substances and transgenic plants capable of synthesising such antipathogenic substances are known, for example, from European patent applications EP 0,392,225 and EP 0,353,191 and International patent application WO 95/33818. The methods of producing such transgenic plants are generally known to the person skilled in the art and are described, for example, in the publications mentioned above.

The methods of the present invention as defined herein are particularly suitable for the treatment of crops grown for agricultural, ornamental, or forestry purposes, in particular, irrigated or flooded crops. In one embodiment, crops are soybean, maize, rice, cotton, vegetables, banana, jatropha, ornamentals, and wheat. More specifically, suitable irrigated crops are soybean, maize, cotton, vegetables and wheat.

Accordingly, in a yet more preferred embodiment, the present invention provides a method of increasing the environmental stress tolerance of an irrigated crop comprising the application of 1-methylcyclopropene in the plant irrigation water, wherein the stress experienced is drought, excessive temperature or frost, or any combination thereof and the plant is soybean, maize, cotton, vegetables, banana or jatropha. Most preferably the stress experienced is drought and the plant is soybean, maize, cotton, vegetables, banana or jatropha.

In a further more preferred embodiment, the present invention provides a method of reducing damage to of an irrigated crop caused by one or more environmental stress factors, comprising the application of 1-methylcyclopropene in the plant irrigation water, wherein the stress experienced is drought, excessive temperature or frost, or any combination thereof. Most preferably the stress experienced is drought and the plant is soybean, maize, cotton, vegetables, banana or jatropha.

In a further more preferred embodiment, the present invention provides a method for improving the quality of an irrigated crop comprising the application of 1-methylcyclopropene in the plant irrigation water, wherein the stress experienced is drought, excessive temperature or frost, or any combination thereof. Most preferably the stress experienced is drought and the plant is soybean, maize, rice, cotton, vegetables, banana or jatropha.

In a further more preferred embodiment, the present invention provides a method for improving the yield of an irrigated crop comprising the application of 1-methylcyclopropene in the plant irrigation water, wherein the stress experienced is drought, excessive temperature or frost, or any combination thereof. Most preferably the stress experienced is drought and the plant is soybean, maize, cotton, vegetables, banana or jatropha.

In a further more preferred embodiment, the present invention provides a method of improving plant vigour of an irrigated crop comprising the application of 1-methylcyclopropene in the plant irrigation water, wherein the stress experienced is drought, excessive temperature or frost, or any combination thereof. Most preferably the stress experienced is drought and the plant is soybean, maize, cotton, vegetables, banana or jatropha.

Normally, for control of biotic stress, a grower in the management of a crop would use one or more other agronomic chemicals in addition to the agrochemicals of the present invention. Examples of agronomic chemicals include pesticides, such as fungicides, herbicides, insecticides, bactericides, acaricides and nematicides, plant nutrients and plant fertilizers.

Accordingly, the present invention provides the methods according to the present invention, which includes the simultaneous and/or sequential application of one or more further agronomic chemicals. Preferably, the one or more further agronomic chemicals are agrochemical compounds and/or plant nutrients and/or plant fertilizers. Preferably, the agrochemical compounds are pesticides, such as fungicides, herbicides, insecticides, bactericides, acaricides and nematicides.

Suitable examples of plant nutrients or plant fertilizers are calcium sulfate $CaSO_4$, calcium nitrate $Ca(NO_3)_2.4H_2O$, calcium carbonate $CaCO_3$, potassium nitrate $KNO_3$, magnesium sulfate $MgSO_4$, potassium hydrogen phosphate $KH_2PO_4$, manganese sulfate $MnSO_4$, copper sulfate $CuSO_4$, zinc sulfate $ZnSO_4$, nickel chloride $NiCl_2$, cobalt sulfate $CoSO_4$, potassium hydroxide KOH, sodium chloride NaCl, boric acid $H_3BO_3$ and metal salts thereof, $Na_2MoO_4$. The nutrients may be present in an amount of 5% to 50% by weight, preferably of 10% to 25% by weight or of 15% to 20% by weight each. Preferred additional nutrients are urea, melamine, potassium oxide, and inorganic nitrates. The most preferred additional plant nutrient is potassium oxide. Where the preferred additional nutrient is urea, it is present in an amount of generally 1% to 20% by weight, preferably 2% to 10% by weight or of 3% to 7% by weight.

Examples of herbicides include glyphosate, glufosinate, glyfosinate, imidazilinone, and STS system (sulfonylurea).

Examples of pesticides include spinosad, avermectin, such as the natural avermectins, A1a, A1b, A2a, A2b, B1a, B1b, B2a and B2b, which can be obtained from *Streptomyces avermitilis*, and avermectin monosaccharide derivatives, such as abamectin, doramectin, emamectin, eprinomectin, ivermectin and selamectin, and milbemycin derivatives, such as milbemectin, milbemycin oxime, moxidectin and SI0009.

Examples of nematicides are abamectin, carbamate nematicides (e.g. aldicarb, carbofuran, carbosulfan, oxamyl, aldoxycarb, ethoprop benomyl, alanycarb), organophosphorus nematicides (e.g. phenamiphos, fenamiphos, fensulfothion, terbufos, fosthiazate, phosphocarb, dichlofenthion, isamidofos, fosthietan, isazofos, ethoprophos, cadusafos, chlorpyrifos, heterophos, isamidofos, mecarphon, phorate, thionazin, triazophos, diamidafos, phosphamidon), methyl bromide, methyl iodide, carbon disulfide, 1,3 dichloropropene, chloropicrin, cytokinins, dazomet, DCIP, ethylene dibromide, GY-81, metam, methyl isocyanate, *Myrothecium verrucaria* composition, flupyrazofos, benchlothiaz, [2-cyanoimino-3-ethylimidazolidin-1-yl]phosphonothioic acid O-ethyl S-propyl ester, and *Bacillus firmus*.

Further suitable examples of pesticides that can be used include acephate, acetamiprid, acetoprole, aldicarb, alpha-cypermethrin, azinphos-methyl, azoxystrobin, benalaxyl, benalaxyl-M, benclothiaz, bendicoarb, benfuracarb, benomyl, bensultap, bifenthrin, bitertanol, boscalid, captan, carbendazim, carbaryl, carbofuran, carbosulfan, carboxin, carbpropamid, chlorothalonil, chlorpyrifos, chlorpyrifos-methyl, clothianidin, copper salts (such as copper sulfate, cuprous oxide, Bordeaux mixture, copper hydroxide, copper sulfate (tribasic), copper oxychloride and copper octanoate), cymoxanil, cypermethrin, cyproconazole, cyprodinil, cyromazine, dazomet, deltamethrin, diazinon, difenoconazole, dimethoate, dimoxystrobin, diniconazole, dinotefuran, Emamectin, endosulfan, ethaboxam, ethirimol, ethiprole, ethoprophos, famoxadone, fenamidone, fenamiphos, fenhexamid, fenpiclonil, fipronil, flonicamid, fluoxastrobin, fluazinam, fludioxonil, fluquinconazole, flutolanil, flutriafol, fonophos, fosetyl-aluminium, fuberidazole, furathiocarb, gamma-cyhalothrin, gamma-HCH, guazatine, heptenophos, hexaconazole, hymexazol, imazalil, imidacloprid, ipconazole, iprodione, isofenphos, lambda-cyhalothrin, mancozeb, maneb, metalaxyl, metalaxyl-M, metconazole, methiocarb, methyl-bromide, methyl-iodide, myclobutanil, nuarimol, omethoate, oxamyl, oxadixyl, oxine-copper, oxolinic acid, pencycuron, pefurazoate, phosmet, picoxystrobin, pirimicarb, prochloraz, procymidone, propamocarb, propiconazole, prothioconazole, pymetrozine, pyraclostrobin, pyrimethanil, pyroquilon, quintozene, silthiofam, spinosad, tebuconazole, tefluthrin, tetraconazole, thiabendazole, thiacloprid, thiamethoxam, thiodicarb, thiophanate-methyl, thiram, tolylfluanid, triadimenol, triazamate, triazophos, triazoxide, triticonazole, trifloxystrobin, 3 Iodo-N*2*-(2-methanesulfonyl-1,1-dimethyl-ethyl)-N*1*-[2-methyl-4-(1,2,2,2-tetrafluoro-1-trifluoromethyl-ethyl)-phenyl]-phthalamide (code NNI-0001), and a compound of 2-Pyridin-2-yl-2H-pyrazole-3-carboxylic acid (2-methylcarbamoyl-phenyl)-amide (code DKI-0001), such as 2-(3-Chloro-pyridin-2-yl)-5-trifluoromethyl-2H-pyrazole-3-carboxylic acid (4-chloro-2-isopropylcarbamoyl-6-methyl-phenyl)-amide, 2-(3-Chloro-pyridin-2-yl)-5-trifluoromethyl-2H-pyrazole-3-carboxylic acid (4-chloro-2-methyl-6-methylcarbamoyl-phenyl)-amide, 5 bromo-2-(3-chloro-pyridin-2-yl)-2H-pyrazole-3-carboxylic acid (4-chloro-2-isopropyl-carbamoyl-6-methyl-phenyl)-amide, 5-Bromo-2-(3-chloro-pyridin-2-yl)-2H-pyrazole-3-carboxylic acid (4-chloro-2-methyl-6-methylcarbamoyl-phenyl)-amide, and 3-difluoromethyl-1-methyl-1Hpyrazole-4-carboxylic acid (2-bicyclopropyl-2-yl-phenyl)amide.

EXAMPLES

The following examples illustrate further some of the aspects of the invention but are not intended to limit its scope. Where not otherwise specified throughout this specification and claims, percentages are by weight (% w/w).

Example 1—Effect of 1-MCP on Stressed Wheat Plants 10 mL of the mixture are added per pouch with a pipette.

20 to 25 Wheat kernels from the variety ARINA were sown in a plastic bag (pouch) with an absorbent paper, watered and grown under optimal conditions in a climate chamber for 8 days. At day 8 the 1-MCP in the form of an α-cyclodextrin molecularly encapsulated powder was applied at a 200 ppm rate to the water in the pouch. After application the plants were not watered anymore, but placed in a warm environment at 26° C. After 5 days without watering the differences of treated vs. untreated were evaluated visually (FIG. 1). Treated plants show greater drought tolerance than control plants when grown under drought stress (5 days without watering).

Examples 2-9—Tomato Epinasty Test

Bioassay test material: 5-6 leaf tomato plants (var. *Rutgers*), 8 reps/treatment.

The first column of table 1 provides a summary of change in angle of the $3^{rd}$ leaf petiole at 24 hours after application of Cerone (ethephon). There are two sets of data, one for those challenged with Cerone at 4 hours after 1-MCP formulation application and a second set for plants challenged with Cerone at 24 hrs after 1-MCP formulation application. Data are the averages of 8 replicate plants

TABLE 1

| | Average change in angle of third petiole | |
|---|---|---|
| Treatment | Cerone applied 4 HAA 1-MCP | Cerone applied 24 HAA 1-MCP |
| (2) Untreated control | −10 | 1 |
| (3) Cerone | 80 | 77 |
| (4) 1 g ai/ha chemigation | 60 | 78 |
| (5) 10 g ai/ha chemigation | 20 | 48 |
| (6) 20 g ai/ha chemigation | −9 | 41 |
| (7) >20 g ai/ha chemigation | −4 | 18 |
| (8) 10 g ai/ha spray | 71 | 82 |
| (9) 20 g ai/ha spray | 40 | 86 |

Notable differences in performance in chemigated vs. spray application were observed.

Procedures Used for Epinasty Test:

1-MCP formulation and rates: 1-MCP in the form of an α-cyclodextrin molecularly encapsulated powder dispersed in an aqueous MgSO4 solution Overhead chemigation in total 0.57 inches irrigation at 1.10 and 20 g ai/ha and wherein >20 g ai/ha chemigation applied in one treatment (incorrect calibration of chemigation pump resulted in >20 g ai/ha rate being applied and reservoir running dry prior to completion of irrigation)

Standard foliar spray at 200 l/ha and 0.035% v/v kinetic silicon adjuvant 0, 10 and 20 g ai/ha Ethephon Treatment:

Application rate 500 g ai/ha at 400 l/ha application volume

Application at 4 and 24 HAA of Invinsa

Epinasty Assessment

Angle of 3rd petiole to plants stem measured prior to 1-MCP application and again at 24 HAT Final data expressed as average change in 3rd petiole angle Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

The invention claimed is:

1. A method of increasing the abiotic environmental stress tolerance, reducing abiotic stress damage, or improving the quality and/or yield and/or vigor of a crop plant under irrigation comprising the application of 1-methylcyclopropene in the form of cyclodextrin molecularly encapsulated powder dispersed in an aqueous $MgSO_4$ solution by chemigation in the plant irrigation water to the crop plant at a rate of 1 to 20 g per hectare and wherein the 1-methylcyclopropene is applied such that the concentration of 1-methylcyclopropene in the irrigation water during application is 100 to 250 ppm.

2. A method according to claim 1 which includes the simultaneous and/or sequential application of one or more further agrochemical compounds and/or plant nutrients and/or plant fertilizers.

3. A method according to claim 2 wherein the further agrochemical compound is a pesticide, such as a fungicide, herbicide, insecticide, bactericide, acaricide or nematicide.

4. A method according to claim 1 wherein the irrigation is localized irrigation, spray irrigation, drip irrigation, bubbler irrigation, micro-sprinkler irrigation, sub-soil irrigation, seepage irrigation, surface irrigation, or manual irrigation, or any combination thereof.

5. A method according to claim 1 wherein the plants are crops selected from soybean, maize, cotton, vegetables, banana, jatropha, ornamentals, and wheat.

6. The method according to claim 1, wherein chemigation is overhead chemigation.

7. A method of increasing the abiotic environmental stress tolerance, reducing abiotic stress damage, or improving the quality and/or yield and/or vigor of a crop plant under irrigation comprising the application of 1-methylcyclopropene in the form of cyclodextrin molecularly encapsulated powder dispersed in an aqueous $MgSO_4$ solution by chemigation in the plant irrigation water to the crop plant at a rate greater than 20 g per hectare and less than 50 g per hectare and wherein the concentration of 1-methylcyclopropene in the irrigation water is 100 to 250 ppm.

8. The method of claim 7, wherein the plant irrigation water is 0.57 inches.

* * * * *